United States Patent [19]

Wollweber et al.

[11] Patent Number: 5,034,408
[45] Date of Patent: Jul. 23, 1991

[54] PESTICIDAL CYCLOPROPANOYLAMINO ACID AMIDE DERIVATIVES

[75] Inventors: Detlef Wollweber, Wuppertal; Gerd Hänssler, Leverkusen, both of Fed. Rep. of Germany

[73] Assignee: Bayer Aktiengesellschaft, Leverkusen, Fed. Rep. of Germany

[21] Appl. No.: 514,918

[22] Filed: Apr. 25, 1990

[30] Foreign Application Priority Data

May 13, 1989 [DE] Fed. Rep. of Germany ....... 3915756

[51] Int. Cl.$^5$ ................. C07D 207/09; C07C 255/52; C07C 235/40; A61K 31/40
[52] U.S. Cl. .................... 514/423; 514/521; 514/616; 548/538; 558/414; 564/155
[58] Field of Search ............... 564/155; 514/616, 423, 514/521; 548/538; 558/414

[56] References Cited

U.S. PATENT DOCUMENTS

| | | | |
|---|---|---|---|
| 3,578,711 | 5/1971 | Largman et al. | 564/155 |
| 4,372,776 | 2/1983 | Day et al. | 558/414 |
| 4,382,954 | 5/1983 | Chan | 564/155 |
| 4,460,603 | 7/1984 | Chan . | |
| 4,537,781 | 8/1985 | Darling | 564/155 |
| 4,570,014 | 2/1986 | Schroder | 564/155 |

FOREIGN PATENT DOCUMENTS

| | | | |
|---|---|---|---|
| 0046707 | 3/1982 | European Pat. Off. | 564/155 |
| 0170842 | 6/1985 | European Pat. Off. . | |
| 2515113 | 10/1975 | Fed. Rep. of Germany . | |
| 3431856 | 3/1986 | Fed. Rep. of Germany | 514/616 |
| 2139837 | 1/1973 | France . | |
| 2072165 | 9/1981 | United Kingdom . | |

Primary Examiner—Glennon H. Hollrah
Assistant Examiner—S. Treanor
Attorney, Agent, or Firm—Sprung, Horn, Kramer et al.

[57] ABSTRACT

Fungicidal cyclopropanoylamino acid amide derivative of the formula

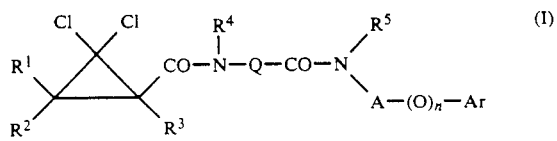

in which
R$^1$, R$^2$, R$^3$, R$^4$ and R$^5$ are identical or different and represent hydrogen or alkyl;
Q represents an unsubstituted or substituted straight-chain or branched alkylene chain, or together with the radical R$^4$ and the nitrogen atom forms a pyrrolidine ring;
A represents a straight-chain or branched alkylene chain;
n represents the number 0 or 1 and
Ar represents unsubstituted or substituted aryl.

14 Claims, No Drawings

PESTICIDAL CYCLOPROPANOYLAMINO ACID AMIDE DERIVATIVES

The present invention relates to new cyclopropanoylamino acid amides, processes for their preparation and their use as agents for combating pests.

The substances according to the invention have an excellent action in combating pests. In particular, the substances according to the invention can be used as fungicides, above all in plant protection.

The present application thus relates to cyclopropanoylamino acid amide derivatives of the general formula

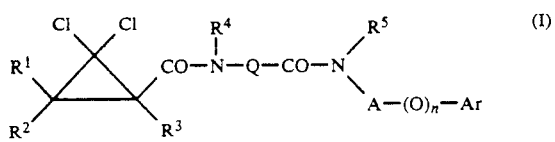

in which $R^1$, $R^2$, $R^3$, $R^4$ and $R^5$ are identical or different and represent hydrogen or alkyl;

Q represents an unsubstituted or substituted straight-chain or branched alkylene chain, or together with the radical $R^4$ and the nitrogen atom forms a pyrrolidine ring;

A represents a straight-chain or branched alkylene chain;

n represents the number 0 or 1 and

Ar represents unsubstituted or substituted aryl.

It has furthermore been found that the new cyclopropanoylamino acid amide derivatives of the formula (I)

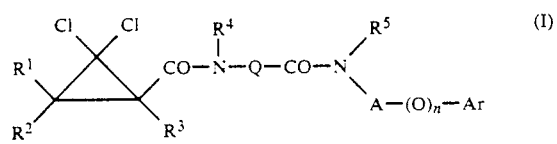

in which $R^1$, $R^2$, $R^3$, $R^4$ and $R^5$ are identical or different and represent hydrogen or alkyl;

Q represents an unsubstituted or substituted straight-chain or branched alkylene chain, or together with the radical $R^4$ and the nitrogen atom forms a pyrrolidine ring;

A represents a straight-chain or branched alkylene chain;

n represents the number 0 or 1 and

Ar represents unsubstituted or substituted aryl, are obtained by a process in which a) a cyclopropanecarboxylic acid of the formula (II)

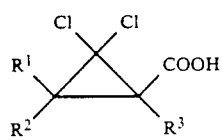

in which $R^1$, $R^2$ and $R^3$ have the abovementioned meanings, or carboxy-activated derivatives thereof, are reacted with an amino acid of the formula (III)

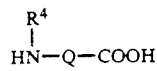

in which $R^4$ and Q have the abovementioned meanings, if appropriate in the presence of a catalyst, if appropriate in the presence of an acid-binding agent and if appropriate in the presence of a diluent, and the resulting cyclopropanoylamino acid of the formula (IV)

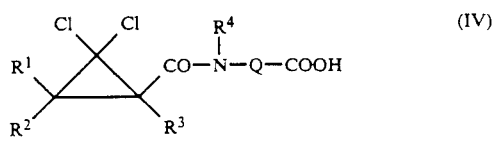

in which $R^1$, $R^2$, $R^3$, and Q have the abovementioned meanings, are then reacted, if appropriate after conversion into a carboxy-activated form, with an amine of the formula (V)

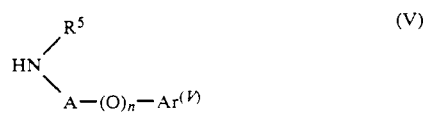

in which $R^5$, A, n and Ar have the abovementioned meanings, if appropriate in the presence of a catalyst, if appropriate in the presence of an acid-binding agent and if appropriate in the presence of a diluent, or b) an amino acid, protected by an amino-protective group, of the formula (VI)

in which $R^4$ and Q have the abovementioned meanings and W represents an amino-protective group, or carboxy-activated derivatives thereof, is reacted with an amine of the formula (V)

in which $R^5$, A, n and Ar have the abovementioned meanings, if appropriate in the presence of a catalyst, if appropriate in the presence of an acid-binding agent and if appropriate in the presence of a diluent, and the resulting amino acid amide of the formula (VII)

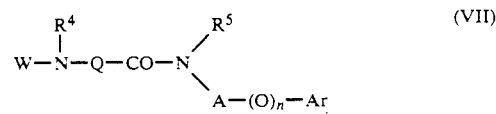

in which

W, $R^4$, Q, $R^5$, A, n and Ar have the abovementioned meanings, is then reacted, after the amino-protective group W has been split off, with a cyclopropane-carboxylic acid of the formula (II)

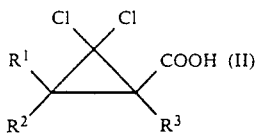

in which $R^1$, $R^2$ and $R^3$ have the abovementioned meanings, or carboxy-activated derivatives thereof, if appropriate in the presence of a catalyst, if appropriate in the presence of an acid-binding agent and if appropriate in the presence of a diluent.

The compounds of the formula (I) can contain one or more chirality centers and can thus be in the form of various enantiomer and diastereomer mixtures which can be separated, if appropriate, in the customary manner. Both the pure enantiomers and diastereomers and the mixtures are claimed according to the invention.

For simplicity, however, they are always referred to below as compounds of the formula (I), although they are understood to include both the pure compounds and the mixtures with different contents of enantiomeric and diastereomeric compounds.

Formula (I) provides a general definition of the compounds according to the invention.

In the general formulae, alkyl, unless defined otherwise, represents straight-chain or branched alkyl having preferably 1 to 8, in particular 1 to 6 and above all 1 to 4 carbon atoms, methyl, ethyl, n- and i-propyl and n-, i-, s- and t-butyl being mentioned as examples and as preferred.

The straight-chain or branched alkylene chain in the definitions of Q preferably contain 1 to 8, in particular 1 to 6 and above all 1 to 4 carbon atoms, methylene, 1,1- and 1,2-ethylene, 1,1-, 1,2-, 1,3--and 2,2-propylene, and 1,1-, 1,2-, 1,3-, 1,4-, 2,2-, 2,3- and 2,4-butylene being mentioned as examples and as preferred.

The alkylene chains can in turn carry one or more, preferably 1 to 3 and in particular 1 or 2 identical or different substituents. Substituents which may be mentioned as examples and as preferred are optionally substituted phenyl and benzyl.

The straight-chain or branched alkylene chain in the definitions of A preferably contain 1 to 6, in particular 1 to 4 and above all 1 to 3 carbon atoms, methylene, 1,1- and 1,2-ethylene and 1,1-, 1,2-, 1,3- and 2,2-propylene being mentioned as examples and as preferred.

Aryl, unless defined otherwise, preferably represents aryl having 6 to 10 carbon atoms which is optionally substituted by one to five identical or different substituents, in particular phenyl or naphthyl which is optionally substituted by one to five and above all one to three identical or different substituents.

Aryl substituents which may be mentioned as examples and as preferred are: halogen, such as fluorine, chlorine, bromine and iodine, in particular fluorine, chlorine and bromine; cyano; nitro; alkyl, alkoxy and alkylthio having preferably 1 to 4 carbon atoms, and above all methyl, ethyl, n- and i-propyl, n-, i-, s- and t-butyl, methoxy, ethoxy, n- and i-propoxy and methylthio; halogenoalkyl, halogenoalkoxy and halogenoalkylthio having preferably 1 to 4 carbon atoms and 1 to 9 identical or different halogen atoms, in particular trifluoromethyl, trifluoromethoxy and trifluoromethylthio; amino; alkylamino and dialkylamino having 1 to 4 carbon atoms, in particular dimethylamino.

Preferred compounds of the formula (I) are those in which $R^1$, $R^2$, $R^3$, $R^4$ and $R^5$ are identical or different and represent hydrogen or straight-chain or branched alkyl having 1 to 6 carbon atoms, Q represents a straight-chain or branched alkylene chain having 1 to 6 carbon atoms which is unsubstituted or substituted by phenyl and/or benzyl, the phenyl and/or benzyl radicals in turn being unsubstituted or substituted by one to three identical or different substituents from the group comprising halogen; cyano; nitro; alkyl and alkoxy having in each case 1 to 4 carbon atoms and halogenoalkyl and halogenoalkoxy having 1 to 4 carbon atoms and 1 to 9 identical or different halogen atoms, or together with the radical R. and the nitrogen atoms forms a pyrrolidine ring, A represents a straight-chain or branched alkylene chain having 1 to 6 carbon atoms, n represents the number 0 or 1 and Ar represents aryl having 6 to 10 carbon atoms which is unsubstituted or substituted by one to five identical or different substituents, possible substituents on the aryl being: halogen; cyano; nitro; alkyl, alkoxy and alkylthio having 1 to 4 carbon atoms; halogenoalkyl, halogenoalkoxy and halogenoalkylthio having 1 to 4 carbon atoms and 1 to 4 identical or different halogen atoms; amino; alkylamino and dialkylamino having 1 to 4 carbon atoms.

Particularly preferred compounds of the formula (I) are those in which $R^1$, $R^2$, $R^3$, $R^4$ and $R^5$ are identical or different and represent hydrogen or straight-chain or branched alkyl having 1 to 4 carbon atoms, Q represents a straight-chain or branched alkylene chain having 1 to 4 carbon atoms which is unsubstituted or substituted by phenyl and/or benzyl, the phenyl and/or benzyl radicals in turn being unsubstituted or substituted by one to three identical or different substituents from the group comprising fluorine, chlorine, bromine, cyano, nitro, methyl, ethyl, n- and i-propyl, n-, i-, s- and t-butyl, methoxy, ethoxy, n- and i-propoxy, trifluoromethyl and trifluoromethoxy, or together with the radical $R^4$ and the nitrogen atom forms a pyrrolidine ring, A represents a straight-chain or branched alkylene chain having 1 to 4 carbon atoms, n represents the number 0 or 1, in particular 0, and Ar represents phenyl or naphthyl which is unsubstituted or substituted t,y one to three identical or different substituents, possible substituents being: fluorine, chlorine, bromine, cyano, nitro, methyl, ethyl, n- and i-propyl, n-, i-, s- and t-butyl, methoxy, ethoxy, n- and i-propoxy, trifluoromethyl and trifluoromethoxy.

If, for example, 2,2-dichloro-1-methyl-cyclopropanecarbonyl chloride, glycine and 4-methylbenzylamine are used as starting substances, the course of process a) according to the invention can be represented by the following equation:

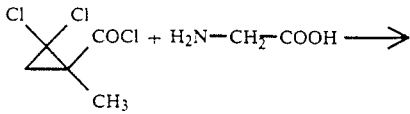

-continued

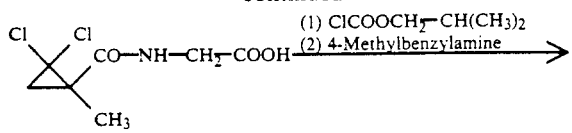

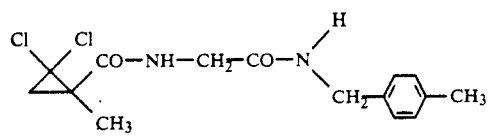

If, for example, t-butyloxycarbonyl-glycine (Bocglycine), benzylamine and 2,2-dichloro-1-methyl-cyclopropanecarbonyl chloride are used as starting substances, the course of process b) according to the invention can be represented by the following equation:

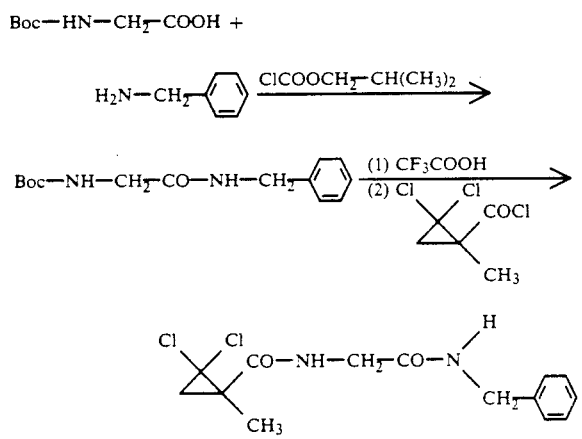

Formula (II) provides a general definition of the cyclopropanecarboxylic acid derivatives to be used for carrying out processes a) and b) according to the invention. In this formula, $R^1$, $R^2$ and $R^3$ preferably have the meanings which have already been mentioned as preferred for these substituents in connection with the description of the substances of the formula (I) according to the invention.

The cyclopropanecarboxylic acid derivatives are known (compare, for example, EP-A-170,842 and DE-OS 2,219,710), or can be obtained by the processes mentioned therein.

Formula (III) provides a general definition of the amino acid derivatives to be used as starting substances for carrying out process (a) according to the invention. In this formula, $R^1$, $R^2$, $R^3$ and X preferably have the meanings which have already been mentioned as preferred for these substituents in connection with the description of the substances of the formula (I) according to the invention.

The amino acid derivatives of the formula (III) are known in some cases (compare, for example, Houben-Weyl, Methoden der organischen Chemie (Methods of Organic Chemistry), Volume XV, Part 1 and 2, Georg Thieme Verlag, Stuttgart 1974; and R.C. Sheppard, A Specialist Periodical Report, Amino acids, Peptides and Proteins, The Royal Society of Chemistry, Burlington House, London 1978, and I. P. Greenstein and M. Winitz, Chemistry of Amino Acids, I. Wiley Sons Inc., New York, London 1961; and E. Schröder and K. Lübke, The Peptides Volume I, Academic Press, New York, London 1965) or can be obtained by the processes described therein.

The amino acid derivatives, protected by an amino-protective group W, of the formula (VI) are likewise known or can be prepared by known processes.

The term "amino-protective group" is generally known (cf., for example: Houben-Weyl, Methoden der organischen Chemie (Methods of Organic Chemistry), Volume XV, Part 1, Georg Thieme Verlag, Stuttgart 1974), and refers to groups which are suitable for protecting (blocking) an amino group from chemical reactions but can easily be removed when the desired reaction elsewhere in the molecule has been carried out. The preferred amino-protective group is tert.-butoxycarbonyl (Boc).

The amino-protective group can be split off in a manner which is known per se by customary methods, for example by solvolysis, such as hydrolysis or acidolysis, by reduction, such as, for example, by hydrogenolysis in the presence of a hydrogenation catalyst or by means of a reduction system of a metal and an agent which splits off protons, it being possible to use various (including different) and selective cleavage methods, depending on the nature of the protective group, if appropriate in the presence of a suitable solvent or diluent or a mixture of these, if desired with cooling, at room temperature or with heating, for example in a temperature range from about $-10°$ C. to the boiling point of the reaction medium, preferably from about $-10°$ C. to about $150°$ C., and if required in a closed vessel, under pressure, in an inert gas atmosphere and/or under anhydrous conditions (cf. Protective Groups in Organic Synthesis, Th. W. Greene, Wiley Interscience, 1981).

The acidolysis is effected, for example, with strong acids, advantageously with trifluoroacetic acid or perchloric acid, but also with other st.rong inorganic acids, such as hydrochloric acid or sulphuric acid, strong organic carboxylic acids, such as trichloroacetic acid or sulphonic acids, such as benzene- or p-toluenesulphonic acid. The presence of an additional inert solvent is possible. Suitable inert solvents are, preferably, organic solvents, for example carboxylic acids, such as acetic acid, ethers, such as tetrahydrofuran or dioxane, amides, such as dimethylformamide (DMF), halogenated hydrocarbons, such as dichloromethane, and furthermore also alcohols, such as methanol, ethanol or isopropanol, as well as water.

Mixtures of the abovementioned solvents are furthermore possible. Trifluoroacetic acid is preferably used in excess without the addition of a further solvent, and perchloric acid is preferably used in the form of a mixture of acetic acid and 70% strength perchloric acid in a ratio of 9:1. The reaction temperatures for these solvolyses are advantageously between about 0 and about $50°$ C., and the reaction is preferably carried out between 15 and $30°$ C. (room temperature).

The Boc group can preferably be split off, for example, with 40% strength trifluoroacetic acid in methylene chloride or with approximately 3 to 5 N hydrochloric acid in dioxane at 15–30° C., and the FMOC group (9-fluorenylmethoxycarbonyl) can preferably be split off with an approximately 5 to 20% strength solution of dimethylamine, diethylamine or piperidine in dimethylformamide at 15–30° C.

Possible carboxy-activated derivatives of the carboxylic acids of the formulae (II), (IV) and (VI) are all the carboxy-activated derivatives, such as acid halides, such as, for example, acid chlorides and acid azides and furthermore symmetric and mixed anhydrides, such as, for example, the mixed 0-alkylcarbonic acid anhydrides, and moreover activated esters, such as, for example, p-nitrophenyl esters or N-hydroxysuccinimide esters, and activated forms of the carboxylic acids produced in situ with condensing agents, such as, for example, dicyclohexylcarbodiimide or carbonyldiimidazole.

The acid chlorides and mixed anhydrides corresponding to the carboxylic acids of the formulae (II), (IV) and (VI) are preferably employed. They can be prepared by reacting the carboxylic acids of the formulae (II), (IV) and (VI) or salts thereof with a halogenating agent or one of the generally known agents for the preparation of mixed anhydrides, such as, for example, phosphorus pentachlcride, thionyl chloride, oxalyl chloride or isobutyl chloroformate, in the generally known manner (cf., for example, Houben-Weyl, Methoden der organischen Chemie (Methods of Organic Chemistry), Volume XV, Part 2, Georg Thieme Verlag, Stuttgart 1974; M. Bodanszky, Principles of Peptide Synthesis, Springer-Verlag, Berlin 1984; and M. Bodanszky, The Practice of Peptide Synthesis, Springer Verlag, Berlin 1984).

The carboxylic acids of the formulae (IV) and (VI) are preferably converted into the carboxy-active mixed anhydrides with alkyl or aryl chloroformates.

The reaction can be carried out in the presence of inert diluents, such as, for example, aromatic, non-aromatic or halogenated hydrocarbons, such as, for example, methylene chloride and toluene; ketones, such as, for example, acetone; esters, such as, for example, ethyl acetate; ethers, such as, for example, tetrahydrofuran; nitriles, such as, for example, acetonitrile or mixtures thereof, and/or in the presence of an acid-binding agent, such as, preferably, a tertiary amine, such as, for example, triethylamine, pyridine or N-methylpiperidine, at temperatures from −78 to 100° C., preferably −60 to 25° C.

Formula (V) provides a general definition of the amines furthermore to be used as starting substances for carrying out processes a) and b) according to the invention. In this formula, $R^5$, A, n and Ar preferably have the meanings which have already been mentioned as preferred for these substituents in connection with the description of the substances of the formula (I) according to the invention.

The amines of the formula (V) are generally known compounds of organic chemistry.

Possible diluents for process (a) according to the invention are inert organic solvents, such as ketones, such as acetone or ethyl methyl ketone; esters, such as ethyl or methyl acetate; amides, such as dimethylformamide; nitriles, such as acetonitrile; chlorohydrocarbons, such as methylene chloride or carbon tetrachloride; hydrocarbons, such as toluene, or ethers, such as tetrahydrofuran, and if appropriate water, and mixtures thereof.

Possible acid-binding agents for process (a) according to the invention are the customary inorganic and organic acid-binding agents. These include, preferably, tertiary amines, such as triethylamine, pyridine or N-methylpiperidine, and inorganic bases, for example metal hydroxides, such as sodium hydroxide and potassium hydroxide, or metal carbonates, such as sodium carbonate or calcium carbonate.

If appropriate, process (a) according to the invention is carried out in the presence of a catalyst. Examples which may be mentioned are 4-dimethylaminopyridine, 1-hydroxy-benzotriazole or dimethylformamide.

The temperatures can be varied within a substantial range in carrying out process (a). The process is in general carried out between −78 to +120° C., preferably at −60 to +40° C.

Equimolar amounts are preferably used for carrying out process (a) according to the invention.

The amino acid derivatives of the formulae (III) and (VI) are employed here as pure optical isomers (D- or L-form) or as racemates.

Equimolar amounts are preferably used for carrying out process (b) according to the invention.

Possible diluents, catalysts and acid-binding agents for process (b) according to the invention correspond to those for process (a).

The cyclopropanoylamino acid derivatives of the formula (IV) which can be isolated as an intermediate product in process (a) according to the invention are known in some cases (DE-OS 2,219,710). These cyclopropanoylamino acid derivatives of the general formula (IV)

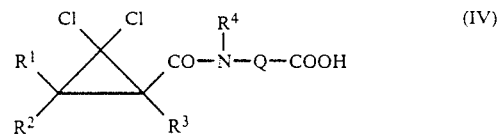

in which
$R^1$, $R^2$, $R^3$ and $R^4$ are identical or different and represent hydrogen or alkyl and
Q represents an unsubstituted or substituted, straight-chain or branched alkylene chain, or together with the radical $R^4$ and the nitrogen atom forms a pyrrolidine ring, excluding the compound in which $R^1$ and $R^2$ represent methyl and $R^3$ and $R^4$ represent hydrogen and Q represents —$CH_2$—, likewise form the subject matter of this application.

The compounds of the formula (IV) can likewise be used for combating pests, in particular as fungicides in plant protection.

In this formula (IV), $R^1$, $R^2$, $R^3$, $R^4$ and Q preferably have the meanings which have already been mentioned as preferred for these substituents in connection with the description of the substances of the formula (I) according to the invention.

The active compounds according to the invention exhibit a potent action against pests and can be used in practice for combating undesirable harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea:*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, Tilletia caries;

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be employed here with particularly good success for combating rice diseases, such as, for example, against the causative organism of rice spot disease (*Pyricularia oryzae*) or against the causative organism of rice stem disease (*Pellicularia sasakii*).

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or. paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospho lipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial z.ange. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1

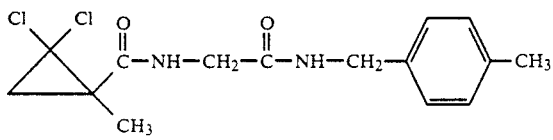

Process a)

4.2 g (0.022 mol) of N-methylpiperidine are added to 5 g of N-(2,2-dichloro-1-methylcyclopropanoyl)-glycine (0.022 mol), dissolved in 55 ml of $CH_2Cl_2$/tetrahydrofuran 9:1, at $-20°$ C. 3.0 g (0.022 mol) of isobutyl chloroformate are then rapidly added dropwise at $-20°$ C., the mixture is subsequently stirred at the same temperature for 10 minutes and cooled to $-60°$ C. and 2.7 g (0.022 mol) of 4-methylbenzylamine are allowed to run in, the temperature being kept below $-15°$ C. After 2 hours at -15° C., the mixture is subsequently stirred at room temperature for 15 hours, the solid is filtered off and subsequently stirred with methylene chloride, the mixture is concentrated, the residue is stirred with water, the colorless solid is filtered off with suction and rinsed first with $NaHCO_3$ solution and then with water and the product is dried in vacuo at 50° C.

6.2 g (85% of theory) of N-(2,2-dichloro-1-methylcyclopropanoyl)-glycine 4-methylbenzylamide of melting point 115–116° C. are obtained.

Preparation of the starting substances

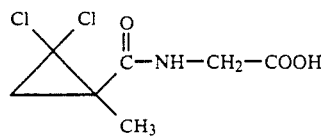

2.0 g (0.027 mol) of glycine are dissolved in 7 ml of 4 N NaOH and 2,2-dichloro-1-methylcyclopropanecarbonyl chloride and 6.5 ml of 4 N NaOH solution are added in portions at 5 to 10° C., while cooling with ice, the pH being kept >8. The mixture is subsequently stirred for 30 minutes, the aqueous phase is extracted twice with ether and acidified to about pH 2 with 1 N HCl and the precipitate formed is filtered off with suction. After drying, 4.5 g (74% of theory) of N-(2,2-dichloro-1-methylcyclopropanoyl)-glycine of melting point 139–140° C. are obtained.

The following compounds of the general formula (IV)

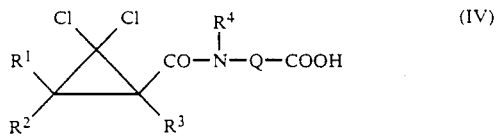

are obtained analogously:

TABLE 1

| No. | $R^1$ | $R^2$ | $R^3$ | $R^4$ | Q | physical data |
|---|---|---|---|---|---|---|
| II | H | H | $CH_3$ | H | $-CH_2-$ | m.p. 139–140° C. |
| III | H | H | $CH_3$ | $CH_3$ | $-CH_2-$ | m.p. 68–70° C. |
| IV | H | H | $CH_3$ | H | $\diagdown\mathrm{CH-CH_3}\diagup$ | NMR δ = 4.2–4.3 ppm |
| V | H | H | $CH_3$ | H | $\diagdown\mathrm{CH-CH(CH_3)_2}\diagup$ | m.p. 166–168° C. |
| VI | H | H | $CH_3$ | H | $\diagdown\mathrm{CH-C_2H_5}\diagup$ | NMR δ = 4.05–4.15 ppm |
| VII | H | H | $CH_3$ | H | $-CH_2-CH_2-$ | NMR δ = 3.0–3.2 ppm |
| VIII | H | H | $CH_3$ | H | $\diagdown\mathrm{CH-CH_2-C_6H_5}\diagup$ | m.p. 150–152° C. |
| IX | H | H | $CH_3$ | H | $\diagdown\mathrm{CH-C_6H_5}\diagup$ | m.p. 156–158° C. |

TABLE 1-continued

| No. | R¹ | R² | R³ | R⁴ | Q | physical data |
|---|---|---|---|---|---|---|
| X | H | H | CH₃ | H | 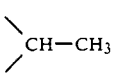 —C(CH₃)₂— | m.p. 215–217° C. |
| XI | H | H | CH₃ | H | —CH₂—CH₂—CH₂— | m.p. 120–122° C. |

EXAMPLE 2

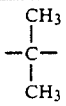

Process b)

2.1 g (0.018 mol) of triethylamine are added to 2 g of glycine benzylamide hydrotrifluoroacetate (0.007 mol), suspended in 60 ml of tetrahydrofuran, at 0 to 10° C. and 1.4 g (0.007 mol) of 2,2-dichloro-1-methylcyclopropanecarbonyl chloride, diluted with 15 ml of tetrahydrofuran, are then added dropwise in the same temperature range. The mixture is stirred at room temperature for 16 hours and concentrated in vacuo, 200 ml of water are added and the precipitate formed is filtered off with suction, washed with dilute HCl, NaHCO₃ solution and water and dried at 50° C. in vacuo.

2.0 g (88% of theory) of N-(2,2-dichloro-1-methylcyclopropanoyl)-glycine benzylamide of melting point 139–141° C. are obtained.

Preparation of the starting substances

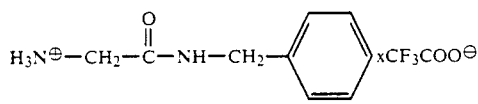

12 g (0.048 mol) of Boc-glycine-benzylamide are stirred in 400 ml of trifluoroacetic acid at room temperature for 1 hour and, after the mixture has been concentrated, the residue is stirred with ether. The colorless solid is filtered off with suction and rinsed with ether and dried over NaOH pellets in a vacuum desiccator.

10.3 g (77% of theory) of glycine benzylamide hydrotrifluoroacetate are obtained (NMR, dimethyl sulphoxide δ=4.35 ppm/7.2–7.4 ppm).

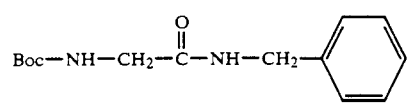 (β)

5.7 g (0.057 mol) of N-methylpiperidine are added to 10 g of Boc-glycine (0.057 mol), dissolved in 100 ml of CH₂Cl₂, at −20° C. and 7.8 g of isobutyl chloroformate (0.057 mol) are then rapidly added dropwise at the same temperature. After 10 minutes at −20° C., the mixture is cooled to −60° C., 6.1 g (0.057 mol) of benzylamine are allowed to run in so that the temperature is kept below −15° C. and the mixture is subsequently stirred at −15° C. for 2 hours and allowed to warm to room temperature. The solid is filtered off and rinsed with CH₂Cl₂, the filtrate is concentrated and water is added to the residue. The oil formed is extracted with ethyl acetate and the ethyl acetate phase is washed with NaHCO₃ solution and water, dried and concentrated.

12 g (84% of theory) of Boc-glycine benzylamide are obtained (NMR, CDCl₃, δ=3.7 ppm/4.4 ppm/1.4 ppm).

The following compounds of the general formula (I)

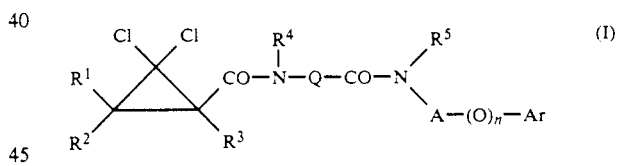 (I)

are obtained in an analogous manner and in accordance with the processes according to the invention.

TABLE 2

| Example No. | R¹ | R² | R³ | R⁵ | R⁴ | Q | A | n | Ar | physical data |
|---|---|---|---|---|---|---|---|---|---|---|
| 3 | CH₃ | CH₃ | H | H | H | —CH₂— | >CH—CH₃ | 0 | —C₆H₄—Cl | |
| 4 | H | H | CH₃ | H | H | —CH₂CH₂CH₂— | —CH₂— | 0 | —C₆H₄—CH₃ | m.p. 128–130° C. |
| 5 | H | H | CH₃ | H | H | —CH₂— | —CH₂— | 0 | —C₆H₄(Cl) | m.p. 119–126° C. |
| 6 | H | H | CH₃ | H | H | —CH₂— | —CH₂— | 0 | —C₆H₄(CH₃) | m.p. 109–112° C. |

TABLE 2-continued

| Example No. | R¹ | R² | R³ | R⁵ | R⁴ | Q | A | n | Ar | physical data |
|---|---|---|---|---|---|---|---|---|---|---|
| 7 | H | H | CH₃ | H | H | —CH₂— | —CH₂— | 0 | 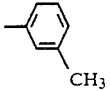 | m.p. 92-93° C. |
| 8 | H | H | CH₃ | H | H | —CH₂— | >CH—CH₃ | 0 | 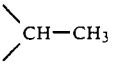 | m.p. 108-113° C. |
| 9 | H | H | CH₃ | H | H | —CH₂— | —CH₂CH₂— | 0 | 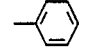 | m.p. 95-97° C. |
| 10 | H | H | CH₃ | H | H | —CH₂— | —CH₂— | 0 | 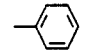 | m.p. 115-116° C. |
| 11 | H | H | CH₃ | H | H | —CH₂— | —CH₂— | 0 | 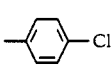 | NMR/DMSO δ: 1.5/4.3/ 7.3-7.4 ppm |
| 12 | H | H | CH₃ | H | H | —CH₂CH₂CH₂— | >CH—CH₃ | 0 | 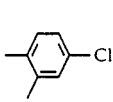 | m.p. 139-141° C. |
| 13 | H | H | CH₃ | H | H | >CH—Ph | >CH—CH₃ | 0 |  | m.p. 200-204° C. |
| 14 | H | H | CH₃ | H | H | >CHCH₂—Ph | >CH—CH₃ | 0 | 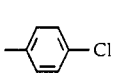 | m.p. 168-170° C. |
| 15 | H | H | CH₃ | H | H | —CH₂CH₂— | >CH—CH₃ | 0 | 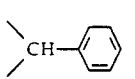 | m.p. 161-163° C. |
| 16 | H | H | CH₃ | H | H | >CH—CH(CH₃)₂ | >CH—CH₃ | 0 |  | m.p. 189-191° C. |
| 17 | H | H | CH₃ | H | CH₃ | —CH₂— | >CH—CH₃ | 0 | 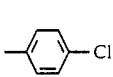 | NMR/DMSO δ: 1.5/ 7.3-7.4 ppm |
| 18 | H | H | CH₃ | H | H | —CH₂— | —CH₂— | 0 |  | m.p. 82-84° C. |
| 19 | H | H | CH₃ | H | H | —CH₂— | —CH₂— | 0 | 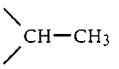 | m.p. 117-120° C. |
| 20 | H | H | CH₃ | H | H | —CH₂— | —CH₂CH₂— | 0 | 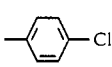 | m.p. 118-121° C. |
| 21 | H | H | CH₃ | H | H | —CH₂— | —CH₂CH₂— | 0 | 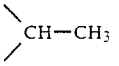 | NMR/DMSO δ: 1.5/3.6-3.7/ 7.2-7.4 |

TABLE 2-continued

| Example No. | R¹ | R² | R³ | R⁵ | R⁴ | Q | A | n | Ar | physical data |
|---|---|---|---|---|---|---|---|---|---|---|
| 22 | H | H | CH₃ | H | H | —CH₂— | —CH₂— | 0 | 2,3-dichlorophenyl | m.p. 123–125° C. |
| 23 | H | H | CH₃ | H | H | —CH₂— | —CH₂— | 0 | 3,5-bis(CF₃)phenyl | m.p. 165–168° C. |
| 24 | H | H | CH₃ | H | H | —CH₂— | —CH₂— | 0 | 3-Cl-4-OCF₃-phenyl | m.p. 97–98° C. |
| 25 | H | H | CH₃ | H | H | —CH₂— | —CH₂— | 0 | 4-SCF₃-phenyl | NMR/DMSO δ: 1.5/4.3/ 7.5–7.6 |
| 26 | H | H | CH₃ | H | H | —CH₂— | —CH₂— | 0 | 4-Cl-phenyl | m.p. 115–118° C. |
| 27 | H | H | CH₃ | H | H | —CH₂— | —CH₂CH₂— | 1 | 4-CH₃-phenyl | m.p. 91–92° C. |
| 28 | H | H | CH₃ | CH₃ | H | —CH₂— | \CH—CH₃ | 0 | phenyl | NMR/DMSO δ: 1.6/4.1/ 7.2–7.4 |
| 29 | H | H | CH₃ | H | H | —CH₂— | \CH₂phenyl | 0 | 4-Cl-phenyl | m.p. 140–142° C. |
| 30 | H | H | CH₃ | H | H | \C(CH₃)₃ | \CH—CH₃ | 0 | 4-Cl-phenyl | m.p. 141–142° C. |
| 31 | CH₃ | CH₃ | CH₃ | H | H | —CH₂— | \CH—CH₃ | 0 | 4-Cl-phenyl | NMR/DMSO δ: 1.1–1.4/ 3.6–3.8/ 7.3–7.4 |
| 32 | H | H | CH₃ | H | H | —CH₂— | \CHCH₃ | 0 | 4-CH₃-phenyl | NMR/DMSO δ: 1.5/3.6–3.7/ 7.0–7.2 |
| 33 | H | H | CH₃ | H | H | —CH₂— | \CH—CH₃ | 0 | 2,4-dichlorophenyl | m.p. 122–124° C. |
| 34 | H | H | CH₃ | H | H | —CH₂— | \CHCH₂CH₃ | 0 | 4-Cl-phenyl | m.p. 152–155° C. |
| 35 | H | H | CH₃ | H | H | —CH₂CH₂CH₂— | \CH—CH₃ | 0 | 4-Cl-phenyl | m.p. 146–151° C. |
| 36 | H | H | CH₃ | H | H | —CH₂— | \CH—CH₃ | 0 | 4-Cl-phenyl | m.p. 114–115° C. |

TABLE 2-continued

| Example No. | R¹ | R² | R³ | R⁵ | R⁴ | Q | A | n | Ar | physical data |
|---|---|---|---|---|---|---|---|---|---|---|
| 37 | H | H | CH₃ | H | H | \CH—C₆H₅ | \CH—CH₃ | 0 | —C₆H₄—Cl (4-) | m.p. 192–193° C. |
| 38 | H | H | CH₃ | H | H | \CHCH₂—C₆H₅ | \CH—CH₃ | 0 | —C₆H₄—Cl (4-) | m.p. 193–197° C. |
| 39 | H | H | CH₃ | H | H | —CH₂CH₂— | \CH—CH₃ | 0 | —C₆H₄—Cl (4-) | m.p. 167–168° C. |
| 40 | H | H | CH₃ | H | H | \CH—CH(CH₃)CH₃ | \CH—CH₃ | 0 | —C₆H₄—Cl (4-) | m.p. 199–201° C. |
| 41 | H | H | CH₃ | H | CH₃ | —CH₂— | \CH—CH₃ | 0 | —C₆H₄—Cl (4-) | NMR/DMSO δ: 1.5/3.1/ 7.3–7.5 |
| 42 | H | H | CH₃ | H | H | —CH₂— | \CH—CH₃ | 0 | —C₆H₄—Cl (2-) | m.p. 155–156° C. |
| 43 | H | H | CH₃ | H | H | —CH₂— | \CH—CH₃ | 0 | —C₆H₄—OCH₃ (4-) | NMR/DMSO δ: 1.5/3 1–3.3/ 7.4 |
| 44 | H | H | CH₂CH₂CH₃ | H | H | —CH₂— | \CH—CH₃ | 0 | —C₆H₄—Cl (4-) | m.p. 106–110° C. |
| 45 | H | H | CH₃ | H | | N(CH₂CH₂)₂CH— | \CH—CH₃ | 0 | —C₆H₄—Cl (4-) | NMR/DMSO δ: 1.5/3.6–3.7/ 7.3–7.2 |
| 46 | H | H | CH₃ | H | H | \CH—CH₃ | \CH—CH₃ | 0 | —C₆H₄—Cl (4-) | m.p. 205–206° C. |
| 47 | H | H | CH₃ | H | H | \CHCH₂—C₆H₅ | \CH—CH₃ | 0 | —C₆H₄—Cl (4-) | m.p. 192–194° C. |
| 48 | H | H | CH₃ | H | H | \CH—CH(CH₃)CH₃ | \CH—CH₃ | 0 | —C₆H₄—Cl (4-) | 192–196° C. |
| 49 | H | CH₃ | CH₂CH₃ | H | H | —CH₂— | \CH—CH₃ | 0 | —C₆H₄—Cl (4-) | NMR/DMSO δ: 0.9/3.6–3 8/ 7.3–7.4 |
| 50 | H | H | CH₃ | H | H | \C(CH₃)CH₃ | \CH—CH₃ | 0 | —C₆H₄—Cl (4-) | 150–151° C. |

TABLE 2-continued

| Example No. | R¹ | R² | R³ | R⁵ | R⁴ | Q | A | n | Ar | physical data |
|---|---|---|---|---|---|---|---|---|---|---|
| 51 | H | H | CH(CH₃)CH₃ | H | H | —CH₂— | \CH—CH₃/ | 0 | —C₆H₄—Cl | NMR/DMSO δ: 1.0–1.1/ 3.5–3.9/ 7.3–7.4 |
| 52 | H | H | CH₃ | H | H | \CHCH₂CH₃/ | \CH—CH₃/ | 0 | —C₆H₄—Cl | p.m. 138–143° C. |
| 53 | H | H | CH₃ | H | H | \CHCH₂CH₃/ | \CH—CH₃/ | 0 | —C₆H₄—Cl | p.m. 140–145° C. |
| 54 | H | H | CH₃ | H | H | \CH—CH₃/ | \CH—CH₃/ | 0 | —C₆H₄—Cl | p.m. 152–157° C. |
| 55 | H | H | CH₃ | H | H | \CH—CH₃/ | \CH—CH₃/ | 0 | —C₆H₄—Cl | p.m. 165–179° C. |
| 56 | H | H | CH₃ | H | H | —CH₂— | —CH₂— | 0 | —C₆H₄—F | p.m. 127–129° C. |
| 57 | H | H | CH₃ | H | H | —CH₂ | \CH—CH₃/ | 0 | —C₆H₄—Cl | p.m. 114–115° C. R-(+) amine |

EXAMPLE

Pyricularia test (rice) / systemic
Solvent: 12.5 parts by weight of acetone
Emulsifier: 0.3 part by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for systemic properties, stan-dard soil in which young rice plants are being grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

The compounds of Preparation Examples 3, 4, 5, 6, 9, 10, 20, 36, 51 and 57 exhibit an excellent degree of action at an application amount of, for example, 100 mg of active compound per 100 cm³.

It will be appreciated that the instant specification and claims are set forth by way of illustration and not limitation, and that various modifications and changes may be made without departing from the spirit and scope of the present invention.

What is claimed is:

1. A cyclopropanoylamino acid amide derivative of the formula

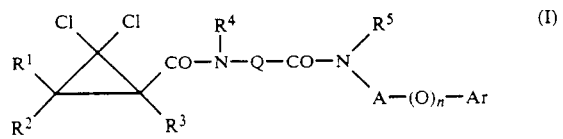

in which

R¹, R², R³, R⁴ and R⁵ are identical or different and represent hydrogen or straight-chain or branched alkyl having 1 to 6 carbon atoms, Q represents a straight-chain or branched alkylene chain having 1 to 6 carbon atoms which is unsubstituted or substituted by phenyl and/or benzyl, the phenyl and/or benzyl radicals in turn being unsubstituted or substituted by one to three identical or different substituents from the group consisting of halogen; cyano; nitro; alkyl and alkoxy having in each case 1 to 4 carbon atoms and halogenoalkyl and halogenoalkoxy having 1 to 4 carbon atoms and 1 to 9 identical or different halogen atoms; or together with the radical R⁴ and the nitrogen atom forms a pyrrolidine ring, A represents a straight-chain or branched alkylene chain having 1 to 6 carbon atoms, n represents the number 0 or 1 and Ar represents aryl having 6 to 10 carbon atoms which is unsubstituted or substituted by one to five identical or different substituents selected from the group consisting of halogen; cyano; nitro; alkyl, alkoxy and alkylthio having 1 to 4 carbon atoms; halogenoalkyl, halogenoalkoxy and halogenoalkylthio having 1 to 4 carbon atoms and 1 to 4 identical or different halogen atoms; amino; alkylamino and dialkylamino having 1 to 4 carbon atoms.

2. A cyclopropanoylamino acid amide derivative according to claim 1, in which $R^1$, $R^2$, $R^3$, $R^4$ and $R^5$ are identical or different and represent hydrogen or straight-chain or branched alkyl having 1 to 4 carbon atoms, Q represents a straight-chain or branched alkylene chain having 1 to 4 carbon atoms which is unsubstituted or substituted by phenyl and/or benzyl, the phenyl and/or benzyl radicals in turn being unsubstituted or substituted by one to three identical or different substituents from the group consisting of fluorine, chlorine, bromine, cyano, nitro, methyl, ethyl, n- and i-propyl, n-, i-, s- and t-butyl, methoxy, ethoxy, n- and i-propoxy, trifluoromethyl and trifluoromethoxy, or together with the radical R and the nitrogen atom forms a pyrrolidine ring, A represents a straight-chain or branched alkylene chain having 1 to 4 carbon atoms, n represents the number 0 or 1, and Ar represents phenyl or naphthyl which is unsubstituted or substituted by one to three identical or different substituents from the group consisting of fluorine, chlorine, bromine, cyano, nitro, methyl, ethyl, n- and i-propyl, n-, i-, s- and t-butyl, methoxy, ethoxy, n- and i-propoxy, trifluoromethyl and trifluoromethoxy.

3. A compound according to claim 1, wherein such compound is N-(2,2,-dichloro-3,3-dimethyl-cyclopropanoyl)glycine 4-chloro-α-methyl-benzylamide of the formula

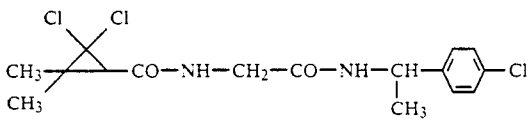

4. A compound according to claim 1, wherein such compound is N-(2,2-dichloro-1-methylcyclopropanoyl)-α-aminobutyryl 4-methyl-benzylamide of the formula

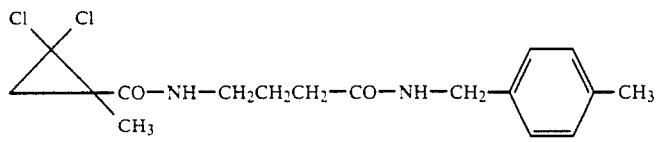

5. A compound according to claim 1, wherein such compound is N-(2,2-dichloro-1-rethylcyclopropanoyl)-glycine 2-chlorobenzylamide of the formula

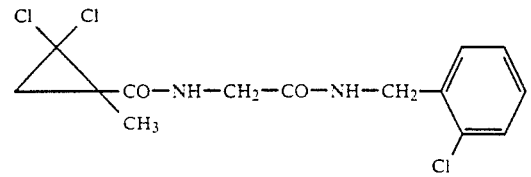

6. A compound according to claim 1, wherein such compound is N-(2,2-dichloro-1- methylcyclopropanoyl)-glycine 2-methylbenzylamide of the formula

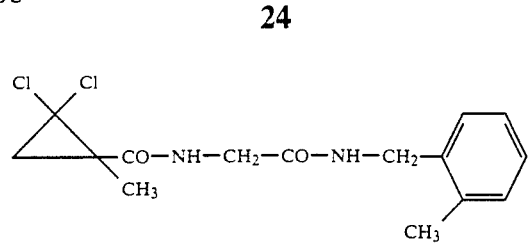

7. A compound according to claim 1, wherein such compound is N-(2,2-dichloro-1- methylcyclopropanoyl)-glycine phenethylamide of the formula

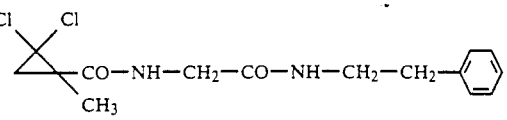

8. A compound according to claim 1, wherein such compound is N-(2,2-dichloro-1-methylcyclopropanoyl)-glycine-4-chlorobenzylamide of the formula

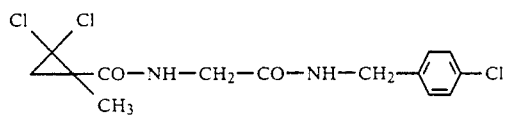

9. A compound according to claim 1, wherein such compound is N-(2,2-dichloro-1-methylcyclopropanoyl)-glycine 2-chlorophenethylamide of the formula

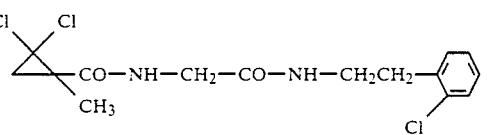

10. A compound according to claim 1, wherein such compound is N-(2,2,-dichloro-1-methylcyclopropanoyl)-glycine 4-chloro -α-methyl-benzylamide of the formula

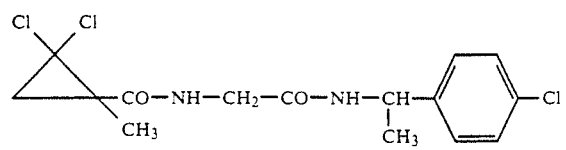

11. A compound according to claim 1, wherein such compound is N-(2,2-dichloro-1-isopropylcyclopropanoyl)glycine 4-chloro-α-methyl-benzylamide of the formula

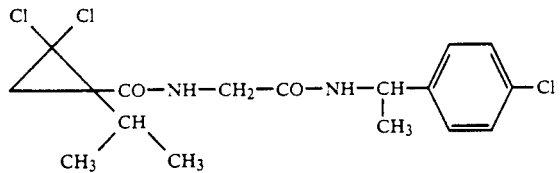

12. A fungicidal composition comprising a fungicidally effective amount of a compound according to claim 1 and a diluent.

13. A method of combating fungi which attack plants which comprises applying to such fungi or to a fungus habitat a fungicidally effective amount of a compound according to claim 1.

14. The method according to claim 13, wherein such compound is

N-(2,2-dichloro-3,3-dimethyl-cyclopropanoyl)glycine 4-chloro-α-methyl-benzylamide,
N-(2,2-dichloro-1-methylcyclopropanoyl)-α-aminobutyl 4-methyl-benzylamide,
N-(2,2-dichloro-1-methylcyclopropanoyl)-glycine 2-chlorobenzylamide,
N-(2,2-dichloro-1-methylcyclopropanoyl)-glycine 2-methylbenzylamide,
N-(2,2-dichloro-1-methylcyclopropanoyl)-glycine phenethylamide,
N-(2,2-dichloro-1-methylcyclopropanoyl)-glycine 4-chlorobenzylamide,
N-(2,2-dichloro-1-methylcyclopropanoyl)-glycine 2-chlorophenethylamide,
N-(2,2-dichloro-1-methylcyclopropanoyl)-glycine 4-chloro-α-methyl-benzylamide, or
N-(2,2-dichloro-1-isopropylcyclopropanoyl)-glycine 4-chloro-α-methyl-benzylamide.

* * * * *

UNITED STATES PATENT AND TRADEMARK OFFICE
CERTIFICATE OF CORRECTION

PATENT NO. : 5,034,408

DATED : July 23, 1991

INVENTOR(S) : Wollweber et al.

It is certified that error appears in the above-identified patent and that said Letters Patent is hereby corrected as shown below:

Col. 22, line 47    Before " represents " insert -- Q --

Col. 23, line 18    Delete " R " and substitute -- $R^4$ --

Col. 23, line 54    Delete " rethylcyclopropanoyl " and substitute -- methylcyclopropanoyl --

Signed and Sealed this

Twenty-seventh Day of April, 1993

*Attest:*

MICHAEL K. KIRK

*Attesting Officer*    *Acting Commissioner of Patents and Trademarks*